United States Patent
Bojanowski et al.

(10) Patent No.: US 10,466,037 B1
(45) Date of Patent: Nov. 5, 2019

(54) SYSTEM AND METHOD FOR CONTROLLING GEAR MOUNTING DISTANCE USING OPTICAL SENSORS

(71) Applicant: Ford Motor Company, Dearborn, MI (US)

(72) Inventors: Paul Bojanowski, Macomb Township, MI (US); Eric Thomas Miller, Dansville, MI (US); Scott Klozik, Berkley, MI (US)

(73) Assignee: Ford Motor Company, Dearborn, MI (US)

( * ) Notice: Subject to any disclaimer, the term of this patent is extended or adjusted under 35 U.S.C. 154(b) by 43 days.

(21) Appl. No.: 15/971,279

(22) Filed: May 4, 2018

(51) Int. Cl.
| | | |
|---|---|---|
| *G01N 21/00* | (2006.01) | |
| *G01B 11/14* | (2006.01) | |
| *G05B 19/27* | (2006.01) | |
| *G01N 21/95* | (2006.01) | |

(52) U.S. Cl.
CPC ......... *G01B 11/14* (2013.01); *G01N 21/9515* (2013.01); *G05B 19/27* (2013.01)

(58) Field of Classification Search
CPC ... H01J 37/32935; G01N 21/64; G01N 21/68; G01N 2015/1037; G01J 3/02
USPC .......................................................... 356/72
See application file for complete search history.

(56) References Cited

U.S. PATENT DOCUMENTS

| | | | |
|---|---|---|---|
| 4,513,539 A * | 4/1985 | Steinback ............... | B24B 21/00 451/300 |
| 5,465,624 A | 11/1995 | Tseytlin et al. | |
| 6,302,764 B1 | 10/2001 | Wirz | |
| 8,411,283 B2 | 4/2013 | Maschirow et al. | |
| 8,567,039 B2 | 10/2013 | Neumaier et al. | |
| 2004/0118235 A1* | 6/2004 | Eldally ................... | F16H 3/426 74/416 |
| 2005/0046850 A1* | 3/2005 | Chow ................ | G01B 11/0625 356/430 |
| 2009/0103081 A1* | 4/2009 | Whelan ..................... | G01J 3/28 356/243.1 |
| 2010/0242283 A1 | 9/2010 | Thompson et al. | |

(Continued)

FOREIGN PATENT DOCUMENTS

| | | |
|---|---|---|
| CN | 103363923 | 10/2013 |
| DE | 102010055820 | 6/2012 |

OTHER PUBLICATIONS

Anca, LaserPlus Measurement System even measures Profile tools, available at URL http://www.anca.com/Resources/Articles/Production-Grinding/LaserPlus-Measurement-System-even-measures-Profile?lang=en-AU.

(Continued)

*Primary Examiner* — Md M Rahman
(74) *Attorney, Agent, or Firm* — Burris Law, PLLC (57) ABSTRACT

The present disclosure is directed toward a system that includes a first optical sensor, a second optical sensor, and a gear feature controller. The first optical sensor measures a plurality of first distances measured from a first reference point to a surface provided between a pair of adjacent teeth among a plurality of teeth circumferentially distributed about a first side of a gear. The second optical sensor measures a plurality of second distances measured from a second reference point to a surface along a second side of the gear opposite the first side. The gear feature controller configured to determine a stock removal amount of the gear based on the first distances and the second distances.

17 Claims, 4 Drawing Sheets

(56) References Cited

U.S. PATENT DOCUMENTS

| | | | | |
|---|---|---|---|---|
| 2011/0032538 A1* | 2/2011 | Maschirow | ........ | G01B 11/2416 |
| | | | | 356/602 |
| 2011/0136408 A1* | 6/2011 | Frazee | ................ | B23F 23/1218 |
| | | | | 451/8 |
| 2015/0038058 A1* | 2/2015 | Frazee | .................... | B23F 23/12 |
| | | | | 451/47 |
| 2018/0128596 A1* | 5/2018 | Mies | .................... | G01B 11/005 |

OTHER PUBLICATIONS

Younes, M.A., et al., Automatic Measurement of Spur Gear Dimensions Using Laser Light, Part 2: Measurement of Flank Profile, available at URL https://www.researchgate.net/publication/243483518_Automatic_measurement_of_spur_gear_dimensions_using_laser_light_part_2_Measurement_of_flank_profile.

\* cited by examiner

SYSTEM AND METHOD FOR CONTROLLING GEAR MOUNTING DISTANCE USING OPTICAL SENSORS

FIELD

The present invention relates to a system and method for finishing a gear surface in accordance with a mounting distance of the gear.

BACKGROUND

The statements in this section merely provide background information related to the present disclosure and may not constitute prior art.

During manufacturing, a gear, such as a ring gear for a vehicular transmission, undergoes a series of operations to form high precision datum surfaces and gear teeth. Generally, gear teeth are machined on a blank material to form an unfinished gear that then undergoes one or more heat treatments to strengthen the material of the gear. Some heat treatments can distort the tooth flanks and the datum of the gear, and therefore, the unfinished gear is hard machined by a machining tool to form the high precision datum surface and gear teeth.

Prior to finishing the gear teeth, the datum surface used to measure a mounting distance of the teeth is hard machined by, for example, a pitch chuck three-jaw chucks, or a device having a bore expansion collet, an outside diameter expansion collet, and an outside diameter chuck. These machining methods can impart clamping errors and inhibit accurate setting of the mounting distance because of the variations between gears and the clamping location. In another machining method, the amount of material to remove is first determined using an over-ball contact technique in which a mounting distance is measured at one or more locations along the unfinished gear. This measurement is then used to determine an average stock removal for the gear. Such technique is time consuming and requires different measurement instruments for different gear tooth geometry. These and other issues are addressed by the teaching of the present disclosure.

SUMMARY

This section provides a general summary of the disclosure, and is not a comprehensive disclosure of its full scope or all of its features.

In one form, the present disclosure is directed to a system that comprises a first optical sensor, a second optical sensor, and a gear feature controller. The first optical sensor is operable to measure a plurality of first distances. Each of the first distances is measured from a first reference point to a surface provided between a pair of adjacent teeth among a plurality of teeth circumferentially distributed about a first side of a gear. The second optical sensor is operable to measure a plurality of second distances measured from a second reference point to a surface along a second side of the gear opposite the first side. The gear feature controller is configured to determine a stock removal amount of the gear based on the first distances and the second distances.

In another form, the gear feature controller calculates a mounting distance based on the first distances and the second distances, and determines the stock removal amount based on the mounting distance.

In one form, the gear feature controller is configured to calculate an average first distance and an average second distance based on the first distances from the first optical sensor and the second distances from the second optical sensor, and determine the stock removal amount based on the average first and second distances.

In yet another form, the first optical sensor and the second optical sensor are operable to perform simultaneous measurements of the first distances and the second distances, respectively.

In one form, a moving mechanism is coupled to the gear and operable to rotate the gear as the first optical sensor and the second optical sensor measure the first distances and the second distances, respectively.

In one form, the system comprises a third optical sensor configured to trigger the first and second optical sensors to measure the first and second distances, respectively.

In another form, the third optical sensor is configured to detect the edge of a tooth to trigger the first and second optical sensors.

In yet another form, the gear feature controller is configured to inspect the gear for one or more undesired characteristics based on the first distances, the second distances, or a combination thereof.

In one form, the undesired characteristics include at least one of missed clamping, high-runout, and geometric defects of a tooth flank.

In yet another form, the system comprises a machining tool, and the first optical sensor and the second optical sensor are arranged with the machining tool. The machining tool is operable to rotate the gear as the first optical sensor and the second optical sensor measure the first distances and the second distances, respectively.

In one form, the machining tool includes a computer numerical control (CNC) machine operable to machine the gear and a machine controller configured to control the CNC machine based on the stock removal amount determined by the gear feature controller.

In one form, the present disclosure is directed toward a method that comprises measuring, by a first optical sensor, a plurality of first distances along a first side of a gear; measuring, by a second optical sensor, a plurality of second distances measured from a second reference point to a datum surface along a second side of the gear opposite the first side; and calculating a stock removal amount based on the first distances and the second distances. Each of the first distances is measured from a first reference point to a surface provided between a pair of adjacent teeth among a plurality of teeth circumferentially distributed about the first side of the gear.

In one form, the method further comprises triggering, by a third optical sensor, the first optical sensor and the second optical sensor to measure each of the first distances and each of the second distances.

In one form, the method further comprises removing, by a machining tool, material from the gear based on the stock removal amount.

In yet another form, the method further comprises clamping the gear in a machining tool equipped with the first optical sensor and the second optical sensor; and positioning, by the machining tool, the gear at predetermined position within a measurement field of the first optical sensor and the second optical sensor.

In one form, the first reference point and the second reference point are defined along a predefined standard profile that is based on a standard gear artifact.

In one form, the present disclosure is directed toward a machining system that comprises a first laser, a second laser, and a controller. The first laser is operable to measure multiple first distances defined between a standard tooth reference and a tooth flank provided between adjacent teeth among multiple teeth distributed about a first side of the gear. The second laser is operable to measure multiple second distances between a standard back reference and a back-face surface of the gear. The controller is configured to calculate a stock removal based on the first and second distances.

In one form, the machining system comprises a machining tool, and the first laser and the second laser are arranged with the machining tool. The machining tool is operable to rotate the gear as the first laser and the second laser measure the first distances and the second distances, respectively.

In one form, the machining tool includes a computer numerical control (CNC) machine operable to machine the gear. The machine controller is configured to control the CNC machine to machine material from the gear based on the stock removal calculated by the gear feature controller.

In one form, the machining system further comprises a third laser configured to trigger the first and second lasers to measure the first and second distances, respectively.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In forming a high precision gear, such as a ring gear for a transmission system, an unfinished gear is clamped in a machining tool, and material is removed from a datum surface that is used to measure a mounting distance defined by the datum surface to a gap between two adjacent teeth. Once the datum surface is finished, the machining tool finishes the gear teeth based on a predefined mounting distance specified for the finished gear. The present disclosure is directed toward a system for locating the machining tool with respect to the datum surface and the gear teeth, and for estimating a stock removal amount for the datum surface. The system utilizes non-contact optical sensors for measuring characteristics related to the gear teeth and the datum surface, and a gear feature controller for estimating a stock removal amount for forming a finished datum surface.

Figure 1:
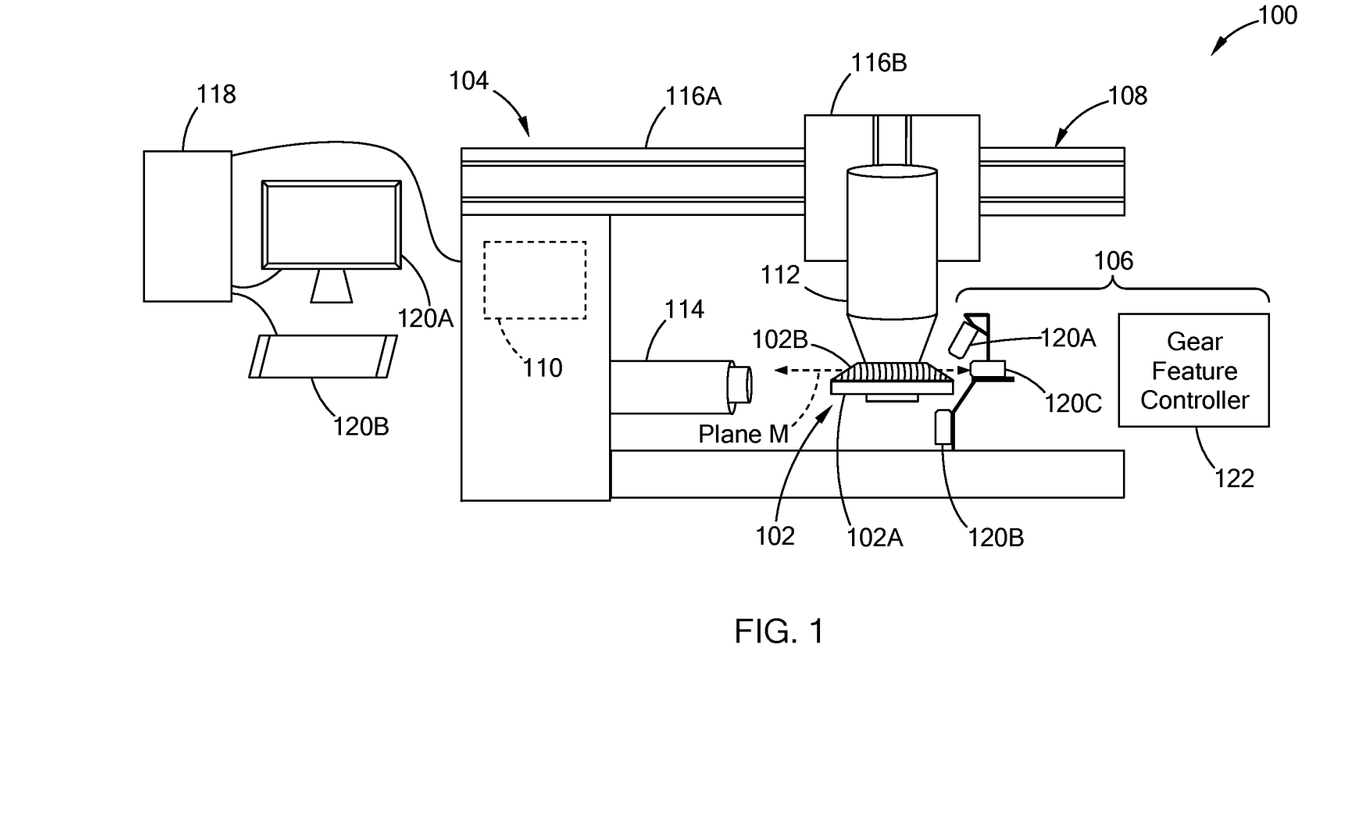
FIG. 1 illustrates a machine system including a mounting distance control tool in accordance with present disclosure.

Referring to FIG. 1, a machine system 100 is operable to remove material from an unfinished gear 102, such as a ring gear, that includes a datum surface 102A on one side and gear teeth 102B on another side of the gear 102 opposite of the datum surface 102A. The system 100 includes a machining tool 104 and a mounting distance control tool 106 ("MDC tool 106"). In one form, the machining tool 104 includes a multi-axis computer numerical control (CNC) machine 108 and a machine controller 110 that controls the CNC machine 108. The teachings of the present disclosure are applicable to other machining tools, and should not be limited to the machining tool 104 depicted in the figure.

In one form, the CNC machine 108 includes an armature 112 for holding the gear 102, and a spindle arm (i.e., spindle) 114 for operating a tool (not shown) to remove material from the gear 102. The armature 112 is operable to rotate the gear 102, and is moveable along one or more axes by way of one or more sliders 116A and 116B. Like, the armature 112, the spindle 114 is also moveable along one or more axes by way of one or more sliders (not shown), such that the armature 112 and the spindle 114 are moveable relative to each other to control the position and alignment of the tool with the gear 102.

In one form, the machine controller 110 includes a processor and a memory for storing computer readable instructions executed by the processor. The machine controller 110 is configured to operate the CNC machine 108 using one or more pre-stored programs executed by the processor. More particularly, along with other components of the CNC machine 108, the machine controller 110 controls the torque, position, orientation, and other operation parameters of the spindle 114 and/or the armature 112 to form the part. The machine controller 110 is accessible by an operator via a computer 118 that includes a user interface, such as a monitor 120A and a keyboard 120B.

The machining tool 104 is operable to hard machine the unfinished gear 102 to form a planar datum surface from which a mounting distance is measured to control a finishing operation of the tooth flanks of the gear 102. As described further herein, the MDC tool 106 locates the position of the datum surface and the gear teeth with respect to a clamping plane of the CNC machine 108, and estimates the amount of material to be removed from the datum surface of the gear.

Figure 2A:
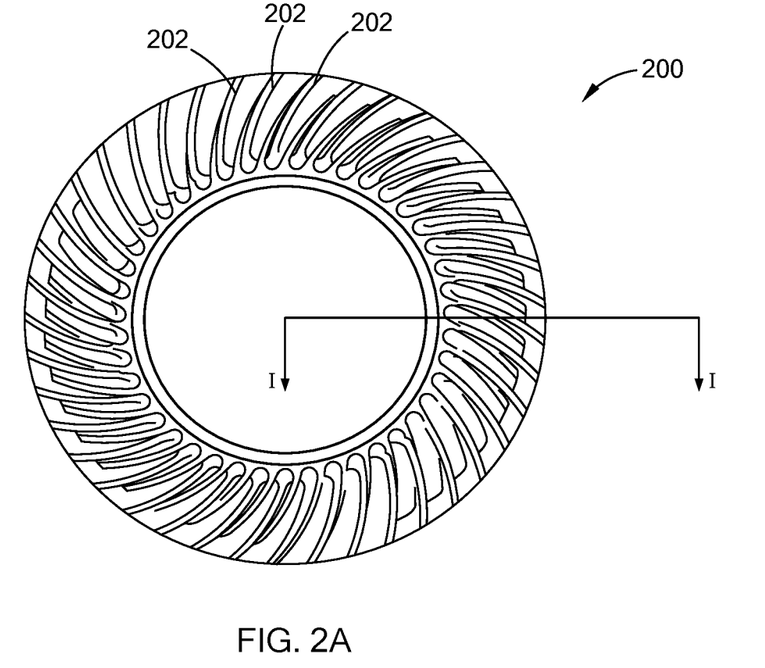
FIG. 2A is a top view of a ring gear in accordance with present disclosure.
Figure 2B:
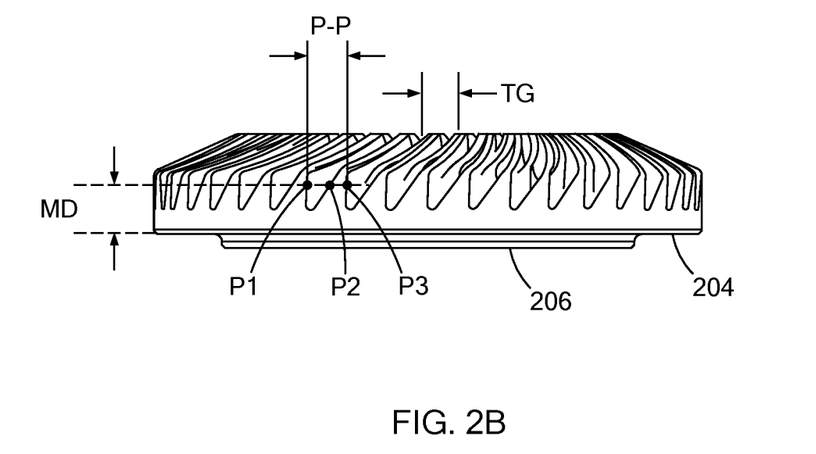
FIG. 2B is a side view of the ring gear of FIG. 2A.
Figure 2C:
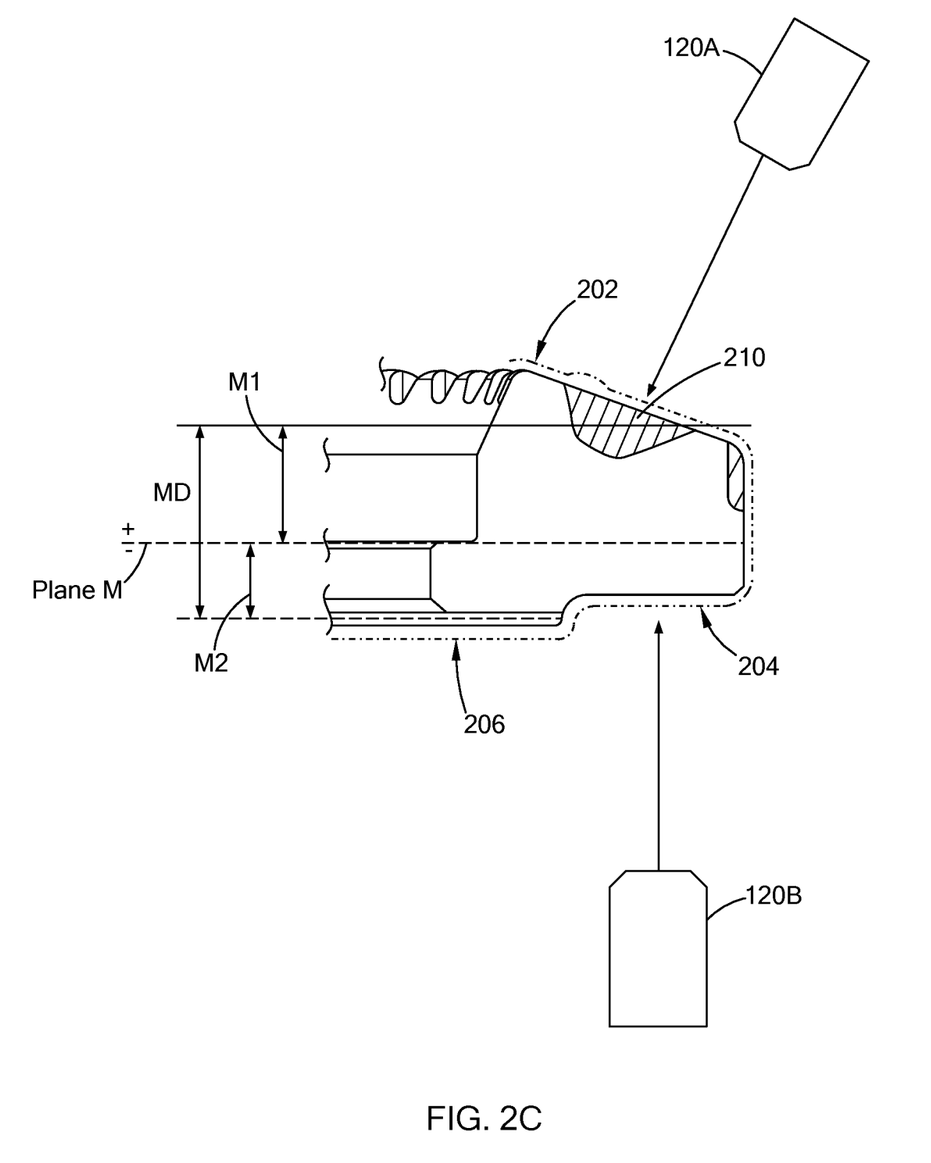
FIG. 2C is a partial cross-sectional view of the ring gear of FIG. 2A taken along line I-I.

More particularly, referring to FIGS. 2A to 2C, a ring gear 200 for an axle assembly is one example of the gear 102 that is finished by the system 100. The ring gear 200 includes a plurality of teeth 202 that are circumferentially distributed along a first side of the ring gear 200, and define a tooth gap (TG) between two adjacent teeth and a pitch-to-pitch distance (i.e., a pitch circle) (P-P) between two adjacent convex pitch points (e.g., distance between P1 and P3 in figure). The gear 200 also defines a back-face surface 204 and a hub surface 206 along a second side of the gear 200 opposite to the first side. The back-face surface 204 is provided as the datum surface from which a mounting distance (MD) is measured to a pitch point (e.g., distance between back-face surface 204 to P1 in figure). As described above, prior to machining, the gear 200 may be slightly distorted, such that the back-face surface is uneven and thus, resulting in a varying mounting distance about the gear 200. For example, in FIG. 2C, an unfinished surface is provided as a dot-dashed line and the standard finished surface is in a solid line. The teachings of the present disclosure is applicable to other types of gear, and should not be limited to the ring gear depicted.

Continuing reference to FIG. 1, the CNC machine 108 is operable to clamp to the gear 150 via the armature 112, and remove material along the back-face surface 102A to form a substantially planar surface. In one form, the CNC machine 108 engages with the gear 150 along a machine reference plane that is perpendicular to an inner diameter surface of the gear 102 (i.e., Plane M). To locate the position of the CNC machine 108 with respect to the back-face surface 102A and the teeth 102B, the MDC tool 106 includes optical sensors 120A, 120B, and 120C (collectively "optical sensors 120"), and a gear feature controller 122 that estimates a stock removal amount based on data from the optical sensors 120.

In one form, the optical sensors 120 are arranged at and mounted with the machine 108. The optical sensors 120 are laser measurement devices to measure or detect a feature along the gear 102. Referring to FIG. 2B, the optical sensor 120A is arranged to measure a flank distance (i.e., a first distance) that is defined between a first reference point to a tooth flank feature 210, such as a pitch surface or rise-to-run surface, between two adjacent teeth 202. The optical sensor 120B is arranged to measure a back-face distance (i.e., a second distance) defined between a second reference point to the back-face surface 204 of the gear 200.

In one form, the optical sensors 120A and 120B are configured to measure true distances defined between the optical sensors 120A and 120B to the flank feature 210 and the back-face surface 204, respectively. In another form, the optical sensors 120A and 120B are configured to measure comparative distances defined between a known standard profile of the gear 200 to the flank feature 210 and the back-face surface 204. More particularly, the optical sensors 120A and 120B are calibrated using an artifact that has a predefined profile, which is captured in the solid outline in FIG. 2C, and a known mounting distance. The distance from the optical sensors 120A and 120B to the respective surface of the artifact is known, and the comparative distances are measured between the predefined profile of the artifact to the flank feature 210 and the back-face surface 204 of the unfinished gear. Accordingly, the predefine profile is configured as the zero difference boundary, such that a surface of unfinished gear 200 that is outside the boundary is a negative distance and a surface that is within the boundary is a positive distance.

To provide accurate measurements, the gear 102 is moved to a predetermined location within a measurement field of the optical sensors 120A and 120B. The optical sensors 120A and 120B measure multiple flank distances and back-face distances, respectively. Specifically, in one form, the armature 112 is operable to rotate the gear 102 as the optical sensor 120A measures the flank distance for each tooth gap, and the optical sensor 120B measures the back-face distance. Accordingly, the armature 112 operates as a moving mechanism.

The flank distance provides a positional relationship between the machine plane (Plane M) to a tooth feature of the unfished gear, and more particularly, is used to determine a distance M1 defined between the tooth gap surface to plane M (FIG. 2C). The base-face distance provides a positional relationship between plane M to the back-face surface, and more particularly, is used to determine a distance M2 defined between plane M to the back-face surface of the unfinished gear. Using distances M1 and M2, the gear feature controller 122 determines the mounting distance (M3) of the unfinished gear as the sum of distances M1 and M2, and compares the mounting distance of the unfinished gear with the predefined mounting distance for the finished gear to estimate a stock removal amount of the gear.

The optical sensor 120C is provided as a trigger device to prompt the optical sensors 120A and 120B to measure the respective distances. In one form, the optical sensor 120C is configured to detect the edge of the tooth and transmit a signal to the optical sensors 120A and 120B to take the measurement as the tooth gap travels through the measurement field.

In another form, in lieu of the optical sensor 120C, the MDC tool 106 is configured in other suitable ways to measure the flank and black-face distances. For example, the MDC tool 106 is configured to track the rotation of the gear 102 and have the optical sensors 102A and 102B provide a continuous measurement of the distances. Using predetermined data, such as the tooth gap, the number of teeth along the gear, and acceptable flank distances, the MDC tool 106 can determines the flank distances and corresponding back-face distances. In another example, using the optical sensor 120A, a pre-defined rise-to-run distance such as 8 mm is determined and identified as a first tooth gap. Using the armature 112, the gear is rotated as the optical sensor 120A and 120B take measurements until the gear makes at least one full revolution. In yet another example, an optical sensor having an internal trigger may be used and/or the gear is controlled to make more than one revolution to obtain additional measurements and then averaging the data to obtain a more accurate measurement.

The gear feature controller 122 is configured to analyze the data from the optical sensors 120 to determine positional information of the unfinished gear, and to estimate a stock removal amount for the back-face surface 204. In one form, the gear feature controller 122 is a controller having a processor and a memory that stores instructions executable by the processor. The gear feature controller 122 is communicably coupled to the optical sensors 120, the machine controller 110, and/or the computer 118 by way of wireless communication link (e.g., Bluetooth, Zig-Bee, Wifi, etc) and/or a wired communication link. In another form, the gear feature controller 122 may be implemented as part of the machine controller, and may not be a separate unit.

To determine the positional information of the gear 102, in one form, the gear feature controller 122 calculates an average flank distance and an average base-face distance by taking the sum of the measurements and dividing the sum by the number of measurements taken. The controller 122 may also be configured to filter the measurement to remove any outlier data points (e.g., omits the lowest and highest measurements taken) before calculating the average distances.

Using the average flank distance and the average base-face distance, the controller 122 adjusts the average values using a predetermined linear aggression model for a particular measurement. For example, the average flank distance is adjusted by multiplying the average flank value with a flank slope factor, which defines the linear relationship between a high and low tooth thickness deviations. Similarly, the average back-face distance is adjusted by multiplying the average value with a datum slope factor that define the linear relationship between a high and low back-face distance variations. The flank slope factor and the datum slope factor are predetermined and unique for each style of gears, such that a gear having 20 teeth with a tooth gap of 10 mm is different from that of a gear having 25 teeth with a tooth gap of 8 mm. The stock removal amount (SRA) is then determined using the following equation in which $FD_{ADJ}$ is the adjusted flank distance, $BD_{ADJ}$ is the adjusted base-face distance, and BC is a bias constant. The bias constant is predefined to adjust (i.e., increase or decrease) the various possible gears mounting distance to improve tooth stock for the final gear tooth finishing. For example, perhaps the finish tooth grind wheel is grinding too much or too little material off near the heel of the tooth because the heat treat distortion shifted. The bias constant is selected to compensate for these shifts in the process. Once calculated, the gear feature controller 122 transmits the stock removal amount and position information (e.g., M1, M2, and/or M3) to have the machine 104 remove material from the back-face surface 102A of the gear 102.

$$SRA=-(FD_{ADJ}+BD_{ADJ}+BC)$$ Equation

In one form, once the CNC machine 104 machines the back-face of the gear, the MDC tool 106 is configured re-inspect the gear to evaluate the mounting distance and provide tracking data or compensation for any tool wear. For example, once machined, the optical lasers measure a finished geometry of the gear. Using the finished geometry, the MDC tool 106 determines if the tool is wearing by comparing the data to predefined standard values. If so, the MDC tool 106 provides additional tool compensation for the next gear to be machined or if the geometry is going beyond a control limit, the machining process may be pause to allow an operator to inspect the tool for damage or wear. In one form, the measurements taken are stored with a 2D matrix on the gear, so that the engineers or subsequent processes can utilize the data for process optimization.

In addition to calculating the positional information and the stock removal, the gear feature controller 122 is also configured to inspect the unfinished gear using the measurements from the optical sensors 120A and 120B. For example, Table 1 defines various undesired characteristics for an unfinished gear and possible actions for addressing such characteristics. In the table, D1 is a flank distance and D2 is a back-face distance. In one form, the gear feature controller 122 is configured to perform one or more of quality checks for assessing the presence of the undesired characteristics, and output the results to the machine controller and/or to the operator by way of the monitor 120A. For example, if a gear is identified as being overly warped, the gear feature controller 122 may output a command to the machine controller 110 to have the machine 108 set aside the unfinished gear and retrieve a new unfinished gear.

TABLE 1

Gear Inspection Check

| Undesired Characteristics | Standard/Test | Countermeasure |
| --- | --- | --- |
| Gear mis-clamped | An average D1 or an average D2 are outside a respective predefined distance, or the multiple D2 measurements encompass a large range of values. | Reposition Gear |
| Gear overly warped | The multiple D1 measurements or the multiple D2 measurements encompass a large range of values. | Set gear aside |
| Root height | Measure distance to the bottom of a tooth using optical sensor and compare to predefined root height to check for defects from the prior tooth cutting operation or severe distortion in the root from heat treatment. | Set gear aside |
| Teeth run-out | A rise-to-run or a rise-to-rise is calculated based on D1 and exceeds a predefined limit. | Set gear aside |
| Tooth gap over/under sizes | D1 rise to run for an individual tooth gap or additional tooth gaps measured after machining are outside a predefined threshold due to inaccurate cutting. | Set gear aside |
| Distance between the flat to outer point chamfer. | Using bottom optical sensor, a line is found within the captured profile that lies in the expected region of a datum weld plane of a finished weld nub feature of the gear. The calculated line can be used to make comparative measurements to other features in the measured profile, such as an intersection point. For example, the intersection of the chamfer (i.e., angled line diverging off of the line of the datum weld plane going to a point that begins a radius). Using the angled line and radius, the intersection of these two features can be calculated. The aligned distance from the datum plane to intersection point can be calculated and compared to a predefined threshold. | Set gear aside |

Figure 3:
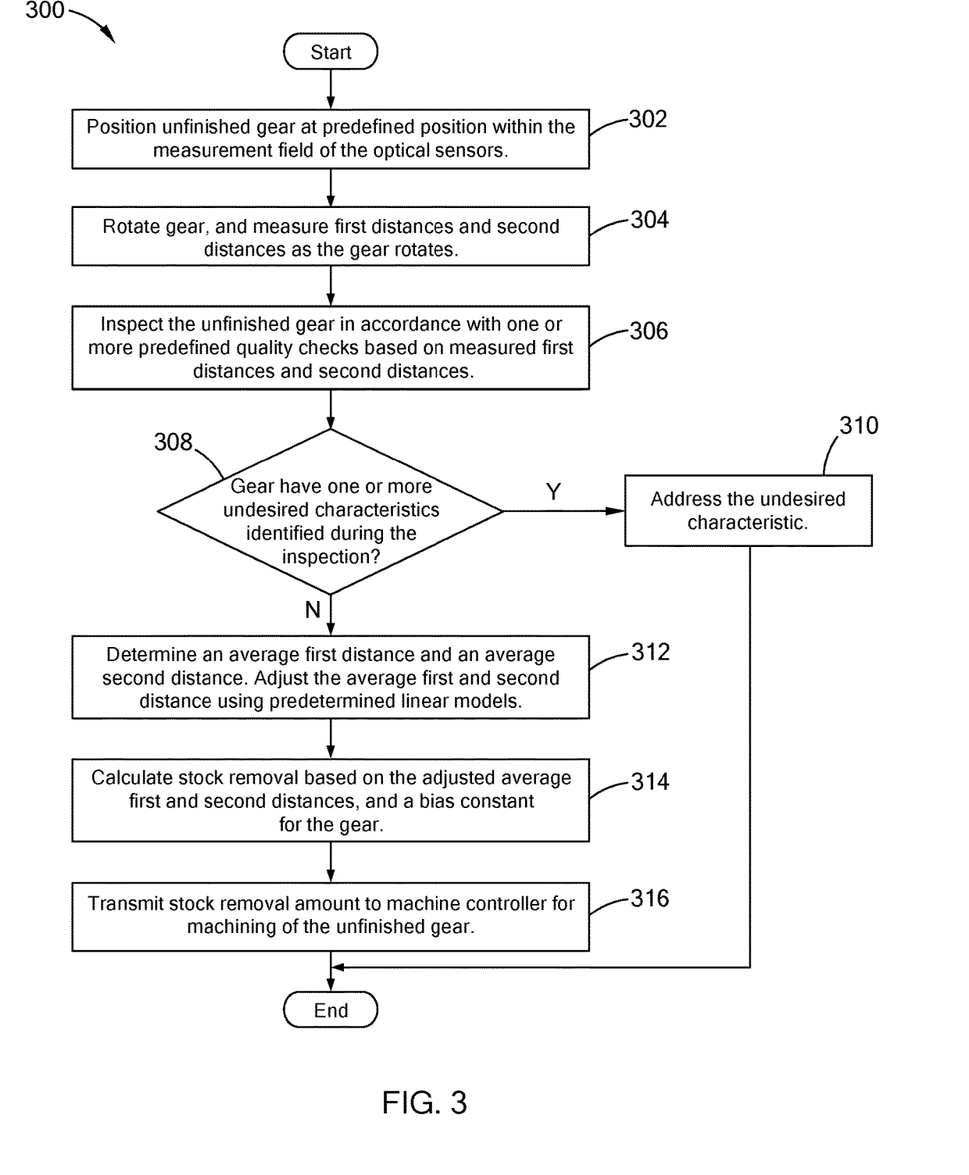
FIG. 3 is a flowchart of a gear mounting control routine in accordance with the teachings of the present disclosure.

Referring to FIG. 3, an example of a gear mounting control routine performed by the mounting distance control tool of the present disclosure. In one form, being in communication with the machine controller, the mounting distance control tool performs the routine when an unfinished gear is clamped by the CNC machine. At 302, the control tool positions the gear at a predefined position within the measurement filed of the optical sensors. For example, the control tool transmits an instruction to the machine controller to move the gear at the predefined location. In another example, the machine controller is configured to automatically move the gear to the predefined location once the gear is clamped, and the control tool is configured to determine whether the gear at the position. At 304, the gear is rotated and the optical sensors measure multiple first distances and multiple second distances, as described above. The optical sensors perform such measurement until the gear is rotated 360-degrees.

At 306, the control tool inspects the unfinished according to one or more quality checks using the measured first distances and second distances, and at 308 determine whether the gear has one or more undesired characteristic based on the inspection. If so, the control tool, at 310, addresses the undesired characteristic using predefined countermeasures associated with the undesired characteristics. If not, the control tool, at 312, determines an average first distance and an average second distance, and adjusts the average first and second distances using predetermined linear models, as described above. At 314, the control unit calculates a stock removal based on the adjusted average first and second distances, and a bias constant of the gear, and transmits the stock removal amount to the machine controller, at 316. Subsequently, the machine controller controls the CNC machine to remove material from the back-face surface of the gear to form a planar datum surface based on the stock removal amount.

The MDC tool of the present disclosure is configured to operate within the machining tool to provide an accurate stock removal amount for an unfinished gear that is clamped by the CNC machine. Using non-contact optical sensors, the MDC tool measures features related to the teeth and the back-face surface of the gear as the gear is being rotated. Accordingly, the MDC tool assess the stock removal amount based on measurement information taken about the entire gear and not at selected locations.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A system comprising:
   a first optical sensor operable to measure a plurality of first distances, wherein each of the first distances is measured from a first reference point to a surface provided between a pair of adjacent teeth among a plurality of teeth circumferentially distributed about a first side of a gear;
   a second optical sensor operable to measure a plurality of second distances measured from a second reference point to a surface along a second side of the gear opposite the first side;
   a gear feature controller configured to determine a stock removal amount of the gear based on the first distances and the second distances; and
   a machining tool including a computer numerical control (CNC) machine operable to machine the gear and a machine controller configured to control the CNC machine based on the stock removal amount determined by the gear feature controller.

2. The system of claim 1, wherein the gear feature controller calculates a mounting distance based on the first distances and the second distances, and determines the stock removal amount based on the mounting distance.

3. The system of claim 1, wherein the gear feature controller is configured to calculate an average first distance and an average second distance based on the first distances from the first optical sensor and the second distances from the second optical sensor, and determine the stock removal amount based on the average first and second distances.

4. The system of claim 1, wherein the first optical sensor and the second optical sensor are operable to perform simultaneous measurements of the first distances and the second distances, respectively.

5. The system of claim 1 further comprising a moving mechanism coupled to the gear and operable to rotate the gear as the first optical sensor and the second optical sensor measure the first distances and the second distances, respectively.

6. The system of claim 1 further comprising a third optical sensor configured to trigger the first and second optical sensors to measure the first and second distances, respectively.

7. The system of claim 6, wherein the third optical sensor is configured to detect the edge of a tooth to trigger the first and second optical sensors.

8. The system of claim 1, wherein the gear feature controller is configured to inspect the gear for one or more undesired characteristics based on the first distances, the second distances, or a combination thereof.

9. The system of claim 8, wherein the undesired characteristics includes at least one of missed clamping, high-runout, and geometric defects of a tooth flank.

10. The system of claim 1, wherein the first optical sensor and the second optical sensor are arranged with the machining tool, and the machining tool is operable to rotate the gear as the first optical sensor and the second optical sensor measure the first distances and the second distances, respectively.

11. A method comprising:
    measuring, by a first optical sensor, a plurality of first distances along a first side of a gear, wherein each of the first distances is measured from a first reference point to a surface provided between a pair of adjacent teeth among a plurality of teeth circumferentially distributed about the first side of the gear;
    measuring, by a second optical sensor, a plurality of second distances measured from a second reference point to a datum surface along a second side of the gear opposite the first side;
    calculating a stock removal amount based on the first distances and the second distances; and
    machining, by a machining tool, the gear based on the stock removal amount determined by the gear feature controller, wherein the machining tool includes a computer numerical control (CNC) machine operable to machine the gear and a machine controller configured to control the CNC machine.

12. The method of claim 11 further comprising triggering, by a third optical sensor, the first optical sensor and the second optical sensor to measure each of the first distances and each of the second distances.

13. The method of claim 11 further comprising:
    clamping the gear in the machining tool equipped with the first optical sensor and the second optical sensor; and
    positioning, by the machining tool, the gear at predetermined position within a measurement field of the first optical sensor and the second optical sensor.

14. The method of claim 11, wherein the first reference point and the second reference point are defined along a predefined standard profile that is based on a standard gear artifact.

15. A machining system comprising:
    a first laser operable to measure multiple first distances defined between a standard tooth reference and a tooth flank provided between adjacent teeth among multiple teeth distributed about a first side of the gear;
    a second laser operable to measure multiple second distances between a standard back reference and a back-face surface of the gear;
    a gear feature controller configured to calculate a stock removal based on the first and second distances; and
    a machining tool including a computer numerical control (CNC) machine operable to machine the gear and a machine controller configured to control the CNC machine based on the stock removal amount determined by the gear feature controller.

16. The machining system of claim 15, wherein the first laser and the second laser are arranged with the machining tool, and the machining tool is operable to rotate the gear as the first laser and the second laser measure the first distances and the second distances, respectively.

17. The machining system of claim 15 further comprising a third laser configured to trigger the first and second lasers to measure the first and second distances, respectively.

* * * * *